US012594113B2

(12) United States Patent
Zhang

(10) Patent No.: US 12,594,113 B2
(45) Date of Patent: Apr. 7, 2026

(54) ABLATION PROBES INCLUDING FLEXIBLE CIRCUITS FOR HEATING AND SENSING

(71) Applicant: Varian Medical Systems, Inc., Palo Alto, CA (US)

(72) Inventor: Hongxuan Zhang, Austin, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 876 days.

(21) Appl. No.: 17/845,647

(22) Filed: Jun. 21, 2022

(65) Prior Publication Data

US 2023/0404648 A1     Dec. 21, 2023

(51) Int. Cl.
*A61B 18/02* (2006.01)
*A61B 18/14* (2006.01)
*A61B 18/00* (2006.01)
*A61B 18/18* (2006.01)

(52) U.S. Cl.
CPC .............. *A61B 18/14* (2013.01); *A61B 18/02* (2013.01); *A61B 2018/00023* (2013.01); *A61B 2018/00577* (2013.01); *A61B 2018/00589* (2013.01); *A61B 2018/0212* (2013.01); *A61B 2018/0243* (2013.01); *A61B 18/1815* (2013.01)

(58) Field of Classification Search
CPC .......... A61B 2018/00023; A61B 18/02; A61B 18/1815; A61B 2018/0212
See application file for complete search history.

(56) References Cited

U.S. PATENT DOCUMENTS 6,540,740 B2    4/2003  Lehmann et al.
7,097,641 B1    8/2006  Arless et al.

8,998,892 B2    4/2015  Winkler et al.
9,717,552 B2    8/2017  Cosman et al.
9,918,772 B2    3/2018  Fischer et al.
2004/0116917 A1  6/2004  Lentz
2004/0215178 A1  10/2004  Maurice
2005/0038422 A1*  2/2005  Maurice ................. A61B 18/02
                                                    606/23
2010/0137857 A1  6/2010  Shroff et al.
2012/0239019 A1  9/2012  Asconeguy
2012/0265186 A1  10/2012  Burger et al.
2012/0265189 A1  10/2012  Davis et al.
2012/0316552 A1  12/2012  Mayse et al.
2013/0324987 A1  12/2013  Leung et al.
2014/0316398 A1  10/2014  Kelly et al.
2015/0045675 A1  2/2015  Chernomorsky
                        (Continued)

FOREIGN PATENT DOCUMENTS

WO       2023249931 A1   12/2023
WO       2023249932 A1   12/2023

OTHER PUBLICATIONS

International Search Report and Written Opinion issued for PCT/US2023/025709 issued Sep. 29, 2023.

*Primary Examiner* — Sean W Collins

(74) *Attorney, Agent, or Firm* — Morgan, Lewis & Bockius LLP; Manita Rawat

(57) ABSTRACT

A probe for performing an ablation treatment includes a shell defining an outer surface and a cryogen supply conduit positioned in the shell. The probe also includes a flexible circuit positioned on at least a portion of the outer surface of the shell. The flexible circuit includes at least one radio frequency (RF) emitter for delivering RF energy to a target tissue.

19 Claims, 6 Drawing Sheets

(56)            References Cited

U.S. PATENT DOCUMENTS

| | | | |
|---|---|---|---|
| 2015/0282859 A1* | 10/2015 | Bencini | A61B 18/02 |
| | | | 606/23 |
| 2016/0331459 A1 | 11/2016 | Townley et al. | |
| 2019/0365451 A1 | 12/2019 | Jung, Jr. | |
| 2020/0030024 A1 | 1/2020 | Rao et al. | |
| 2022/0133381 A1* | 5/2022 | Prologo | A61B 5/6852 |
| | | | 606/21 |
| 2023/0371997 A1 | 11/2023 | Zhang et al. | |

* cited by examiner

100

ABLATION PROBES INCLUDING FLEXIBLE CIRCUITS FOR HEATING AND SENSING

FIELD

The present disclosure relates to treatment probes including flexible circuitry. More particularly, the present disclosure relates to ablation probes that allow for radio frequency (RF) and/or cryo ablation treatments using flexible circuitry integrated into or onto the probes.

BACKGROUND

This section provides background information related to the present disclosure which is not necessarily prior art.

Systems and methods for providing ablation treatments generally include the introduction of a probe at or near a target tissue in a patient. The target tissue may be an abnormal or undesirable tissue such as a tumor. The ablation treatment is performed to destroy the target tissue. In addition to destroying the target tissue, it is desirable to minimize damage or harm to healthy tissues that may be located near to the target tissue.

One type of ablation treatment is a cryoablation treatment. Cryoablation treatments may include cryoablation probes that are introduced at or near the target tissue in the patient. A cryoablation system may include an extremely cold cryogen (liquid, gas, or mixed phase) that may be passed through the probe in thermal contact with the target tissue. Heat from the tissue passes from the tissue, through the probe, and into the cryogen that removes heat from the targeted tissue. This removal of heat causes tissue to freeze, resulting in the destruction of the targeted tissue. When the tissue freezes, ice forms typically in an iceball. The iceball may be in the form a sphere, ellipsoid or other shape. It is desirable to perform cryoablation treatments such that the target tissue is completely frozen and that the freezing of surrounding tissues and/or body structures is minimized.

In other treatments, radio frequency (RF) energy can be used to ablate a target tissue and/or provide pain relief. A probe may be inserted at or near a target tissue in a patient during such treatments. The probe may emit or deliver radio frequency energy to the target tissue. In some examples, the radio frequency energy can heat the target tissue to an elevated temperature that may destroy the tissue. In other examples, the radio frequency energy may be delivered to provide pain relief to an affected region or target tissue.

Traditional or existing probes and methods suffer from various drawbacks. Some of these drawbacks may result from the extreme temperatures that are used to produce the iceballs during the cryoablation freezing cycles or the elevated temperatures used in RF ablation treatments. For example, it can be difficult to bring tissue temperatures back to more moderate temperatures following the freezing cycle. The time required to heat tissue and/or bring tissue to moderate temperatures can be longer than may be desirable. Furthermore, it can be difficult to incorporate heaters, electrical contacts, leads and other elements into probes and maintain a size that can be used to cause minimal impact on the patient. There exists a need, therefore, for improved ablation probes and methods that integrate cryo, radio frequency (RF), and sensing functionality into a suitably sized device.

SUMMARY

This section provides a general summary of the disclosure, and is not a comprehensive disclosure of its full scope or all of its features.

In various embodiments of the present disclosure, apparatuses and methods for performing ablation treatments are provided. The apparatuses and methods may include improvements directed to ablation probes and ablation systems. In some embodiments, the ablation probes may include a flexible circuit. The flexible circuit may include various electrical elements to provide radio frequency (RF) treatments and to obtain measurement data. The flexible circuit can be positioned on outside of the shell of the probe. The probes with such flexible circuits are improvements over existing probes and related methods because the circuitry and electrical elements can be positioned closely together and can include complex circuitry otherwise not possible using existing or traditional structures. The flexible circuitry disposed on the shell of the probe also allows room for a cryogen supply conduit internal to the probe that can be configured to provide cryo ablation treatments. Thus, the probes and methods of the present disclosure can provide combination cryo RF treatments and other heating and RF cycles that are not available on existing and traditional devices.

In some embodiments of the present disclosure, an ablation probe is provided. The probe may include a shell defining an outer surface, a cryogen supply conduit positioned in the shell, and a flexible circuit positioned on at least a portion of the outer surface of the shell.

In one aspect, the flexible circuit may include at least one radio frequency (RF) emitter configured to deliver RF energy to a target tissue.

In another aspect, the flexible circuit may include a plurality of measurement points configured to obtain measurement data during the ablation treatment.

In another aspect, the flexible circuit may include a plurality of heaters.

In another aspect, the flexible circuit covers at least about 50% of the exterior surface of the probe.

In another aspect, the external surface of the shell is exposed between portions of the flexible circuit.

In another aspect, the flexible circuit may include an RF emitter configured to thaw an iceball formed during a freezing cycle of the ablation treatment.

In another aspect, the flexible circuit may include an RF emitter configured to perform a coagulation treatment of a bleeding condition.

In another aspect, the flexible circuit is a first flexible circuit positioned at a first axial position on the shell and the probe may include a second flexible circuit positioned at a second axial position on the shell.

In another aspect, the cryogen supply conduit defines an inflow for a cooling path, and the outer surface of the supply conduit and an inner surface of the shell defining the outflow path.

In another aspect, the cryogen supply conduit is configured to move liquid or gaseous nitrogen through the probe.

In another aspect, the flexible circuit may include a plurality of RF electrodes.

In another aspect, the probe may include a microwave antenna.

In some embodiments of the present disclosure, an ablation system is provided. The ablation system may include an ablation controller coupled to the probe. The ablation controller may include at least one processor configured to deliver a cryogen to the cryogen supply conduit and to deliver an RF signal to and RF emitter on the flexible circuit.

In some embodiments of the present disclosure, a method of performing an ablation treatment is provided. The method may include delivering a cryogen to a probe to perform a freezing cycle of an ablation treatment, obtaining measurement data from one or more measurement points on a flexible circuit on the probe, and delivering a radio frequency (RF) signal to an RF emitter on the flexible circuit.

In one aspect, the steps of the method are performed during a common treatment.

In another aspect, the radio frequency (RF) emitter may include an RF electrode.

In another aspect, the radio frequency (RF) emitter is a heater.

In another aspect, the step of delivering the RF signal may include performing a coagulation treatment.

In another aspect, the step of delivering the RF signal may include ablating the target tissue.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
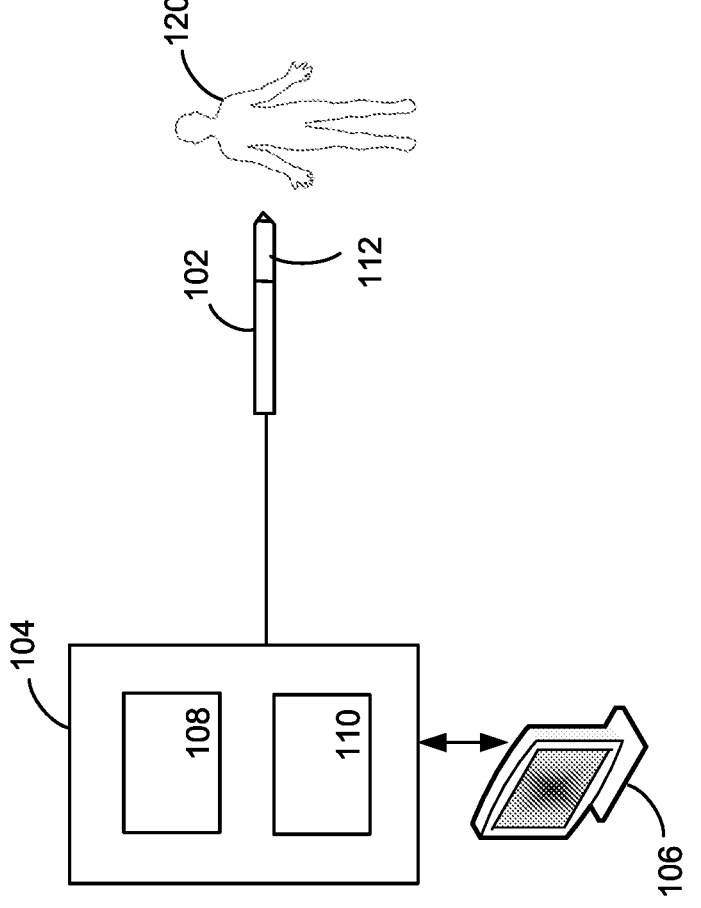
FIG. 1 is a diagram illustrating an example ablation system in accordance with some embodiments of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In some embodiments of the present disclosure, an ablation probe is provided that includes a flexible circuit. The flexible circuit may provide various functionality to the probe. The flexible circuit, in some embodiments, may include heating circuits, radio frequency (RF) emitters, measurement points and other electrical elements that can be used in connection with an ablation treatment. The flexible circuit may allow tissue to be heated in a region at which the probe is located to provide ablation treatment, pain relief, localized heating, coagulation, and the like. The flexible circuit may also provide sensing functionality to obtain measurements of conditions or operating parameters of the probe such as temperature at one or more locations along the probe.

In some embodiments, the probe may include cryo ablation functionality in addition to heating and/or radio frequency (RF) functionality. The probe may include a cooling path that can allow a cryogen (e.g., nitrogen, argon, oxygen, etc.) to flow to cause ice to form at a target tissue during a freezing cycle of a cryoablation treatment. The flexible circuit can, in turn, provide thaw, RF ablation, coagulation or other functionality that may be used in connection or in addition to the cryo treatment.

In still other embodiments, the aforementioned probes can be incorporated into an ablation system that may provide cryo ablation treatments, radio frequency (RF) treatments, and/or combination RF-cryo treatments. The ablation systems may include a controller and/or computing device to allow receive measurement data from the flexible circuit on the probe and deliver signals to the flexible circuit to cause heating or other functionality to be performed at the target tissue.

The systems, probes and methods of the present disclosure are improvements over existing or traditional systems, devices, and methods by providing functionality that is not possible using existing systems. Still further the flexible circuits of the present disclosure can provide increased functionality over existing devices and can be incorporated in a suitably or desirably sized ablation probe to minimize the impact of the treatment on a patient. Still further, the flexible circuits of the present disclosure can be configured in various ways to provide variable functionality as may be desirable depending on the conditions and need of the patient and the related treatment.

Turning now to FIG. 1, an example ablation system 100 is shown. The ablation system 100, in one example, may include an ablation controller 104, a probe 102, and an ablation computing device 106. The probe 102 may be coupled to the ablation controller 104 to provide operation in both a cryo mode and a radio frequency (RF) mode. The ablation controller 104 may include a cryo delivery system 108 and a RF delivery system 110 that will be further described.

The cryo delivery system 108 can deliver a cryogen to the probe 102. The cryogen can remove heat from the probe and from tissue that may be located near the probe 102 when the probe 102 is positioned in a desired location in the patient 120. The probe 102 may be positioned, for example, at or near a target tissue such as a tumor, lesion, or other abnormal tissue. The cryo delivery system 108 can cause an iceball (of various suitable shapes and sizes) to be produced at a distal end of the probe 102 that destroys the target tissue. The cryogen may be various suitable fluids. In one example, the cryo delivery system 108 is configured to deliver liquid and/or gaseous nitrogen, argon, or oxygen to the probe 102.

The RF delivery system 110 can be configured to deliver RF energy to the probe 102. The RF delivery system 110 can deliver an electrical current, for example, to the probe 102 that can be transferred to the surrounding tissue of the patient 120 via one or more RF electrodes on a flexible circuit 112. The flexible circuit 112 can be fixed on the probe 102 in a suitable position at or near a distal end of the probe 102. The RF electrodes on the flexible circuit 112 can be positioned at or near a distal end of the probe 102. In this manner, the RF energy can be transferred to the target tissue and, in turn, heat the tissue at the distal end of the probe 102. The heat can be produced using various duty cycles and/or via various power profiles to elevate the temperature of the tissue to destroy the tissue, coagulate a bleeding condition, and/or return the turn the tissue a normal body temperature as may be desired.

The flexible circuit 112 may also include one or more measurement points. The measurement points may include electrical pads that can measure a temperature, impedance, pressure, or other characteristic of the patient, the ablation system 100, and/or other conditions during an ablation treatment. The flexible circuit 112 may also include suitable sensors that can act as measuring points for the collection of information during an ablation treatment. The measurement points can be connected to the ablation controller 104 that can collect, analyze, store, and/or perform other operations with the information from the measurement points.

In other examples, the probe 102 may include a microwave antenna. The antenna may be positioned at the distal end of the probe 102. The RF delivery system 110 can deliver a current to the antenna (via a coaxial cable in the probe, for example) to cause microwaves to be emitted. The microwaves, in turn, can heat the tissue at or near the distal end of the probe 102 to destroy tissue, coagulate a bleeding condition, and/or return the tissue to a normal body temperature. In still other examples, the RF electrodes and/or the microwave antenna may be used to treat a pain condition in the patient via delivery of the RF energy. In the present disclosure, the term RF emitter is used to describe various structures that use RF energy to heat tissue at the distal end of the probe 102. Such various structures may include RF electrodes, microwave antennas and the like.

The ablation system 100 may also include the ablation computing device 106 that is coupled to the ablation controller 104. While the ablation controller 104 and the ablation computing device 106 are shown as separate elements in FIG. 1, it should be appreciated that these elements (and other elements) may be combined into single structures or be further separated from that shown and described.

The ablation computing device 106 may include various suitable processing devices such as a computer, server, laptop, tablet, workstation, circuit, or the like to provide the functionality described. The ablation computing device 106 may also include a display and/or other input-output devices to allow a user to interact, control, view, and otherwise configure the operation of the ablation system 100.

The ablation system 100 may include other elements or be configured in other manners in other examples. The ablation system 100 may be configured as a combination RF-cryo ablation system in some examples and can be operated to perform combination RF-cryo ablation treatments. Further details of such example combination RF-cryo ablation computing devices are described in U.S. patent application Ser. No. TBD entitled Apparatuses and Methods for Combination Radio Frequency and Cryo Ablation Treatments filed on the same day as the present application to Varian Medical Systems, Inc. The contents of the aforementioned patent application is incorporated by reference herein in its entirety.

Figure 2:
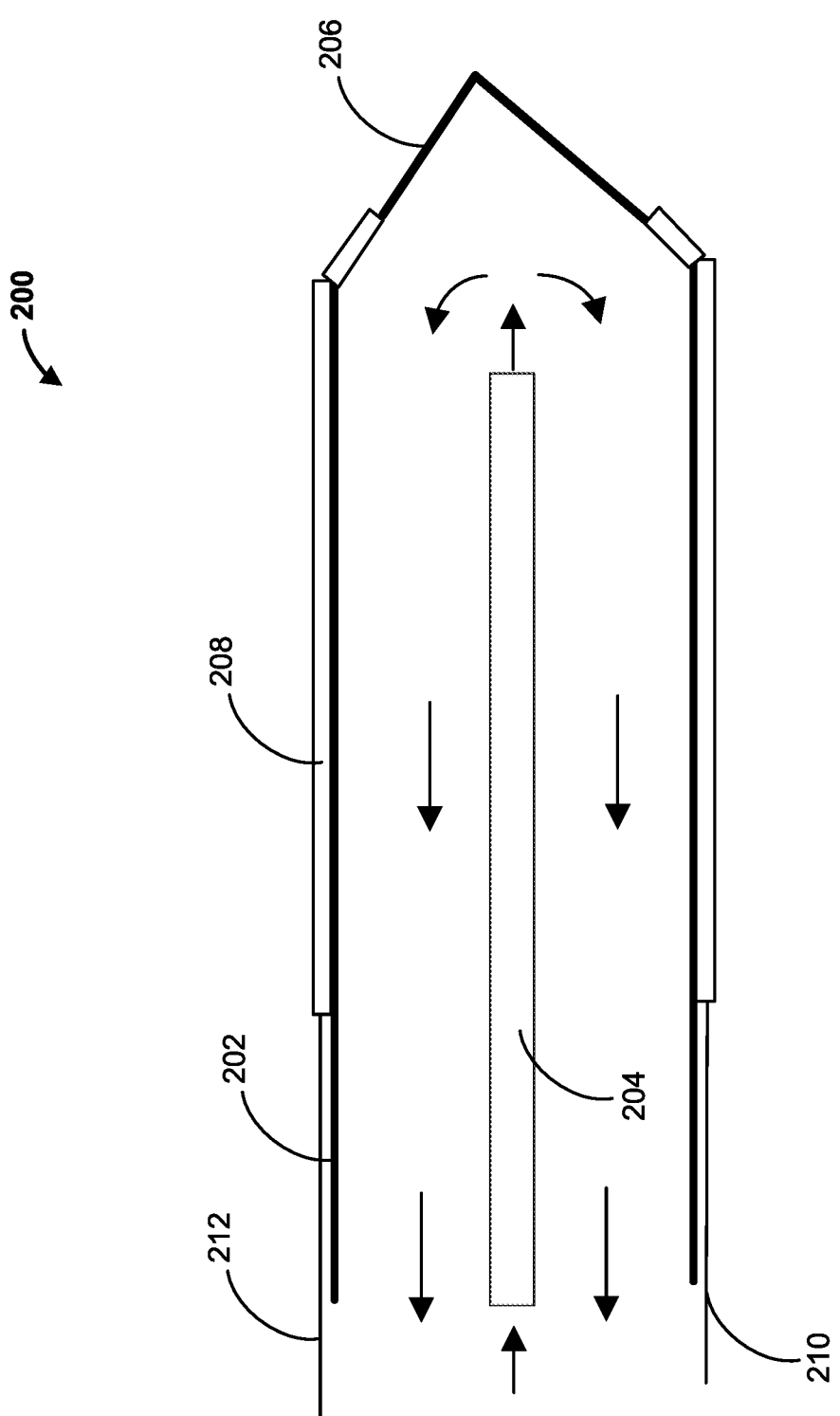
FIG. 2 is a side view illustrating an example probe including a flexible circuit in accordance with some embodiments of the present disclosure.

Referring now to FIG. 2, an example probe 200 is shown. The probe 200 can be used in an ablation system such as the ablation system 100 previously described. The probe 200 includes a flexible circuit 208. The flexible circuit 208 can be positioned on the external surface of the shell 202 of the probe 200. The probe 200 may be, for example, an ablation probe made of a stainless steel or other suitable material. The shell 202 can be a cylindrically shaped member that is hollow to include other elements of the probe that will be hereinafter described. The flexible circuit 208 can be secured to the external surface of the shell 202 using a suitable adhesive, epoxy or other material. The flexible circuit 208 can be secured at or near the distal end 206 of the probe 200.

The flexible circuit 208 can include measurement points, electrical pads, electrodes, sensors, heaters, RF electrodes, connecting leads, and other electrical elements that can be used to perform one or more of the functions described herein. The flexible circuit 208 can be made via various suitable manufacturing methods and may have various layers of conductive and non-conductive materials to allow the circuitry to be located at various locations along the axial length of the probe and circumferentially around the exterior of the probe. The flexible circuit 208 may be configured as a flexible planar member and then wrapped and secured around the exterior surface of the shell 202. In other examples, the flexible circuit 208 may be configured as a sleeve that is positioned over the shell 202 and then secured in a desired position.

The flexible circuit 208 may be configured, for example, as a flexible printed circuit board (PCB) circuit. Such a circuit may use a bendable polyimide substrate to insulate and protect conductive copper layers that connect electronic components of the flexible circuit. The flexible circuit 208 may have a thickness in a range of about 0.05 mm to about 0.6 mm. In other examples, other thickness may be used. The flexible circuit 208 may be made using one or more conductive layers separated by one or more dielectric or insulating layers. An adhesive and/or epoxy may be used to join the various layers of the flexible circuit 208 together. The layers of the flexible circuit may be laser cut or etched to allow electronic components to be soldered or otherwise joined to the conducting layers of the flexible circuit 208.

Referring back to FIG. 2, the flexible circuit 208 may be electrically coupled to the ablation controller 104 (FIG. 1) via one or more leads 212, 210. Each of the sensors, pads, electrodes, heaters or other electrical elements may be joined to the ablation controller 104 via a lead. The leads 210, 212 may be a suitable electrical wire or conductor to pass electrical signals and/or current from and to the ablation controller 104. As shown, the leads 210, 212 may be positioned along an outer surface of the shell 202. In other examples, the leads 210, 212 can be embedded or joined to the shell 202 or be router through the shell 202 or through the internal cavity of the shell 202.

As further shown, the probe 200 may include a cryogen supply 204. The cryogen supply 204 may be fluidly connected to a source of cryogen (not shown) that can supply the cryogen via a pump, valve or other elements. Such elements may be part of and/or connected to the cryogen delivery system to supply cryogen to the probe 200. The cryogen may flow along a cryogen path in the probe 200. The cryogen path may include a cryogen inflow that is defined by the interior of the cryogen supply 204. The cryogen path may also include a cryogen outflow defined by an interior surface of the shell 202 and an outer surface of the cryogen supply 204. The cryogen may flow in through the cryogen supply and flow out of the probe 200 along the cryogen outflow. The flow of cryogen can remove heat from the target tissue at which the probe 200 may be positioned during an ablation treatment.

With both the flexible circuit 208 and the cryogen path, the probe 200 may be configured to operate in either a RF mode of operation and/or a cryo mode of operation to provide freezing cycles and/or heating cycles during an ablation treatment. In some examples, the cryo system of the probe 200 and the flexible circuit 208 of the probe 200 can be operated at the same time. For example, when the probe is performing a freezing cycle, the flexible circuit 208 may be operated to heat portions of the probe 200 to shape the iceball in a desired manner. Furthermore, the flexible circuit 208 may be operated during a freezing cycle to collect measurement data, such as temperature data, via one or more measurement points located on the flexible circuit.

The flexible circuit 208 can be configured as a single integrally formed circuit that can be fixed to the probe 200. In other examples, the flexible circuit 208 can be multiple individual flexible pieces that are fixed to the probe 200 and electrically coupled to each other and/or to the ablation controller.

Figure 3:
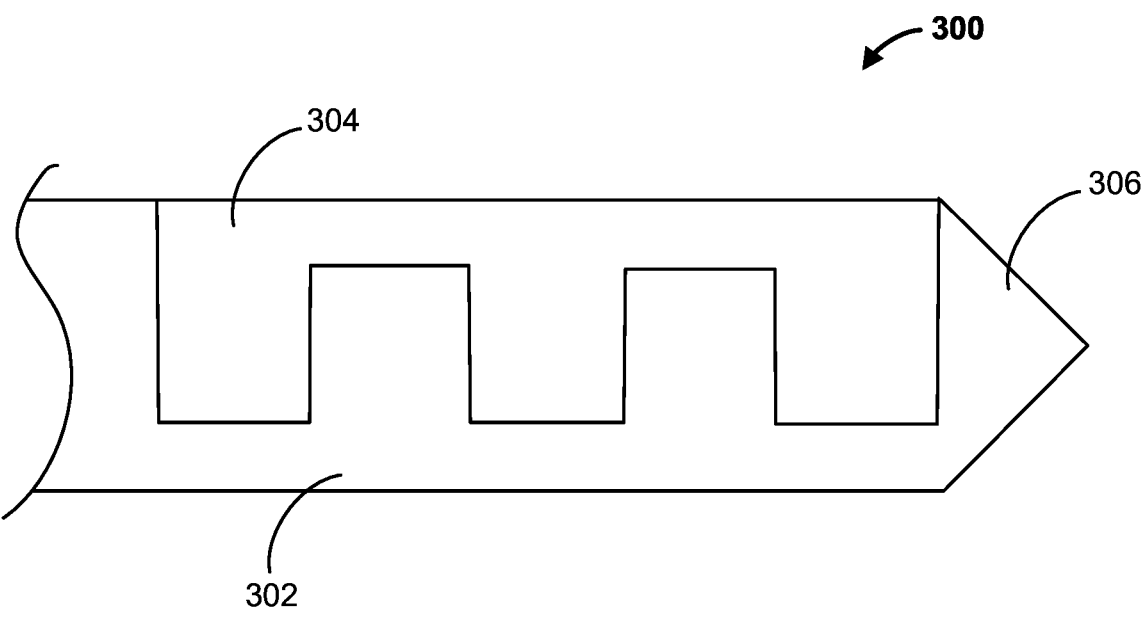
FIG. 3 is a side view of an example probe illustrating an example flexible circuit in accordance with some embodiments of the present disclosure.
Figure 4:
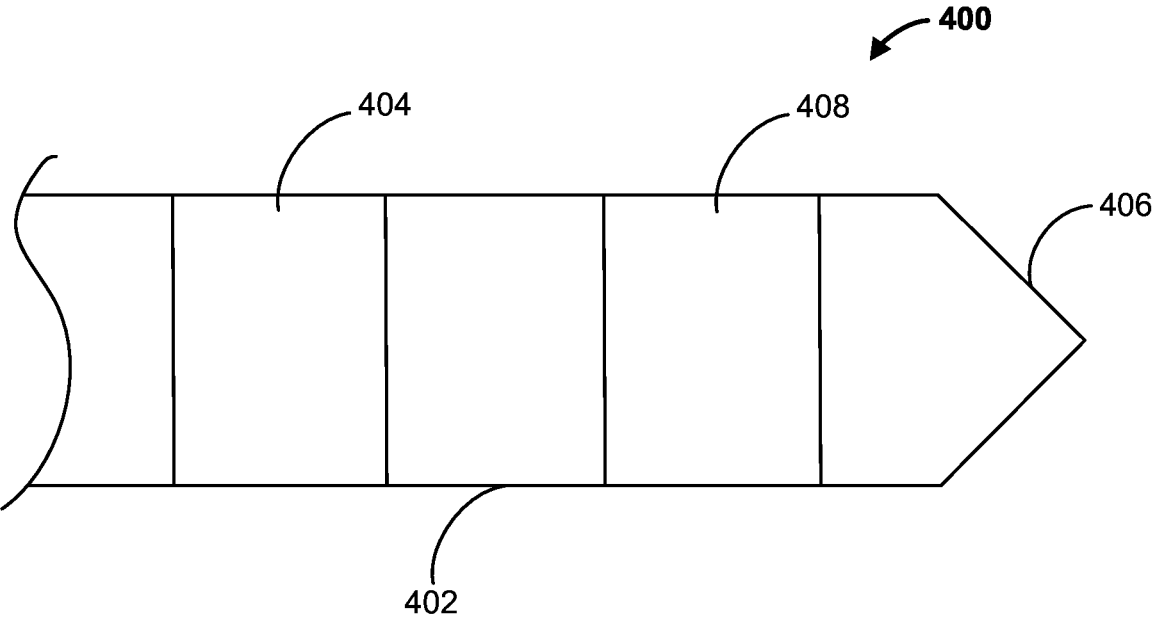
FIG. 4 is a side view of an example probe illustrating another example flexible circuit in accordance with some embodiments of the present disclosure.

Referring now to FIGS. 3 and 4, alternate embodiments of flexible circuit are shown. In the example shown in FIG. 3, the probe 300 may include a flexible circuit 304. As shown, the flexible circuit 304 may be configured to have a shape that does not cover the entire outer surface of the shell 302. The flexible circuit may have cut-outs, openings, or a discontinuous outer profile to allow portions of the shell 302 to be exposed between portions of the flexible circuit 304. Such a flexible circuit 304 may be used, for example, to allow portions of the shell 302 to contact the target tissue during an ablation treatment. Such a configuration may be desirable to improve the efficiency of heat transfer through the shell 302 during a freezing cycle. In configurations in which the flexible circuit 304 is provided over the entire outer surface, heat transfer may be inhibited to a degree by the flexible circuit.

In another example as shown in FIG. 4, a probe 400 may include multiple flexible circuits. In this example, the probe 400 includes a first flexible circuit 404 and a second flexible circuit 408. The first flexible circuit 404 can be located at a different axial position than the second flexible circuit 408. In addition, the first flexible circuit 404 may be spaced apart from the second flexible circuit 408 to expose a portion of the shell 402 between the flexible circuits.

The examples of FIGS. 3 and 4 show two alternatives but many other configurations can also be used. The flexible circuit may have circular, square, rectangular, or other shaped holes and/or may have other outer profiles to allow portions of the shell of the probe to be exposed between or adjacent to portions of the shell covered by the flexible circuit. The flexible circuit may have various extensions, fingers, or other shapes to position electrical components such as heaters, leads, pads, electrodes, sensors or the like at desired positions along the shell of the probe at various circumferential and/or axial positions relative to the tip of the probe. In various examples, the flexible circuit may be configured to cover a portion of the entire outer surface area of the shell. In some examples, the flexible circuit may be configured to cover less than 100% of the surface area of the shell. In another example, the flexible circuit may be configured to cover about 50-75% of the surface area of the shell. In still another example, the flexible circuit may be configured to cover about 50% of the surface area of the shell. In yet other examples, other coverages can also be used. In determining such coverages, the percentage can be performed by determining a total surface of the shell of the probe from the tip to a predetermined distance from the tip. A surface of the flexible circuit can be determined relative to the total surface of the shell along the same axial distance from the tip.

Figure 5:
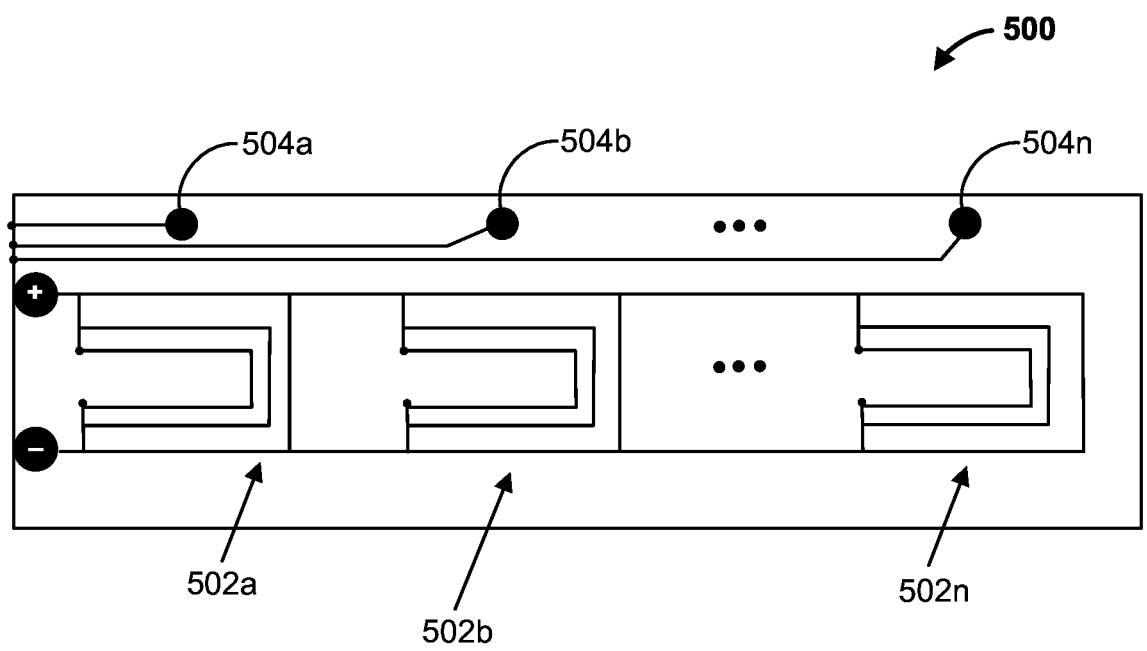
FIG. 5 is an illustration showing an example flexible circuit that may be used on a probe in accordance with some embodiments of the present disclosure.

Referring now to FIG. 5, an example flexible circuit 500 is shown. The flexible circuit 500 can be configured as previously described to be positioned along an outer surface of a probe. The flexible circuit, in this example, includes a plurality of electrical pads 504a, 504b, to 504n. The flexible circuit 500 can be of various suitable lengths and can include electrical pads in a number of 1 to n. The pads 504 may be spaced along the flexible circuit 500 and can be coupled to the ablation controller to provide various functionality. For example, the pads 504 may be configured as a thermocouple, thermistor, pressure sensor, radio frequency (RF) lead, impedance sensor, RF power discharge pad, or the like. The pads, therefore, may provide various functionality such as measurement collection, heating, RF treatment, coagulation, pain treatment, ablation, and the like.

The flexible circuit 500 may also include one or more heaters 502a, 502b, to 502n. The heaters 502 may be configured as a resistive heater and may have various patterns to provide localized heating at the heaters 502. The flexible circuit 500 can include various quantities of heaters in a number of 1 to n. In some examples, the heaters 502 can be evenly spaced along a length of the flexible circuit 500. In other examples, the heaters 502 can be positioned to provide heating a desired area of the probe. The heaters 502 may be electrically coupled to the ablation heater and controlled to provide heating that may provide coagulation, thaw, ablation, or the like.

Figure 6:
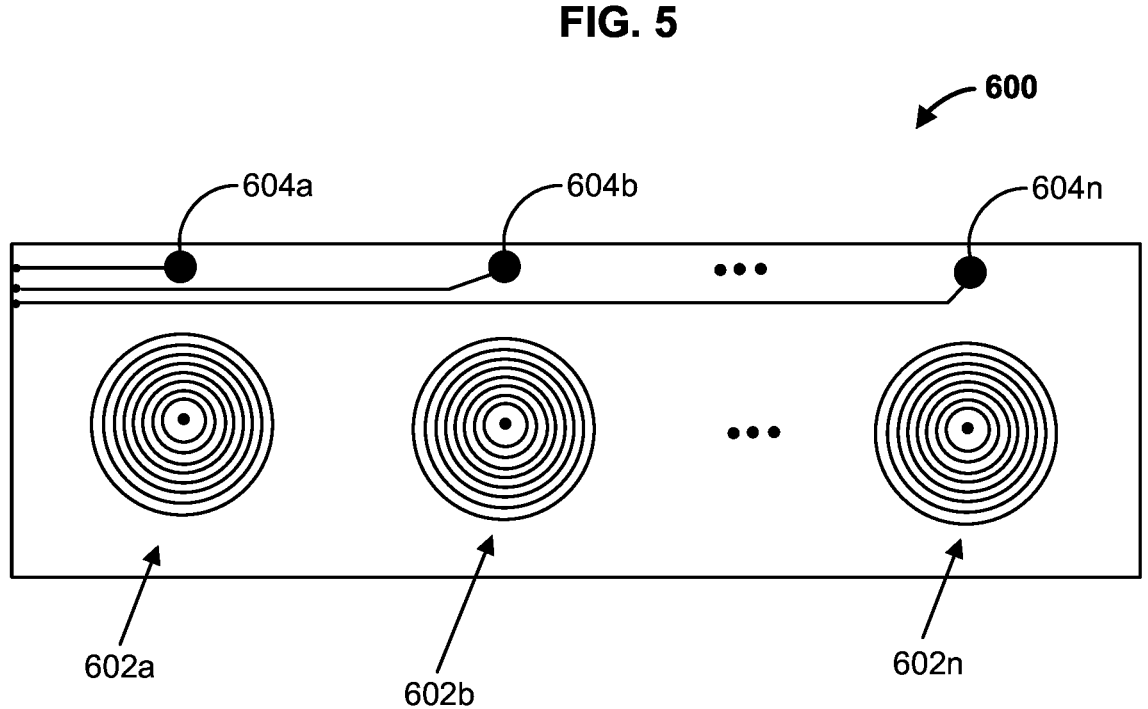
FIG. 6 is an illustration showing another example flexible circuit that may be used on a probe in accordance with some embodiments of the present disclosure.

Another example flexible circuit 600 is shown in FIG. 6. The flexible circuit 600 may be similar to the flexible circuit 500 in that the flexible circuit 600 may include one or more pads 604. The flexible circuit 600 may have a number of pads from 1 to n. The pads 604 may be similar and may have similar functions and structure as the pads 504 previously described. The example flexible circuit 600 may also include one or more heaters 602. The flexible circuit 600 may include any suitable number of heaters 602. The flexible circuit 600 may include any suitable number of heaters from 1 to n. The heaters 602 may be positioned along the flexible circuit 600 to provide heating and functionality as previously described with respect to heaters 502 of circuit 500. In this examples, the heaters 602 may be coupled to an ablation controller and/or a power supply via a wireless energy transferring. The heaters 602 can use external RF emission power to convert the wireless signal to heat and/or power for energy discharge.

The examples shown in FIGS. 5 and 6 show example configurations of flexible circuits. In other examples, other variations and configurations can also be used. In various examples, the flexible circuits may include multiple rows of pads, multiple rows of heaters. In other examples, the pads and heaters can be staggered, alternated, and/or positioned in various arrays to provide heating, sensing, stimulation, ablation, pain relief, or the like as may be desired in various locations.

Figure 7:
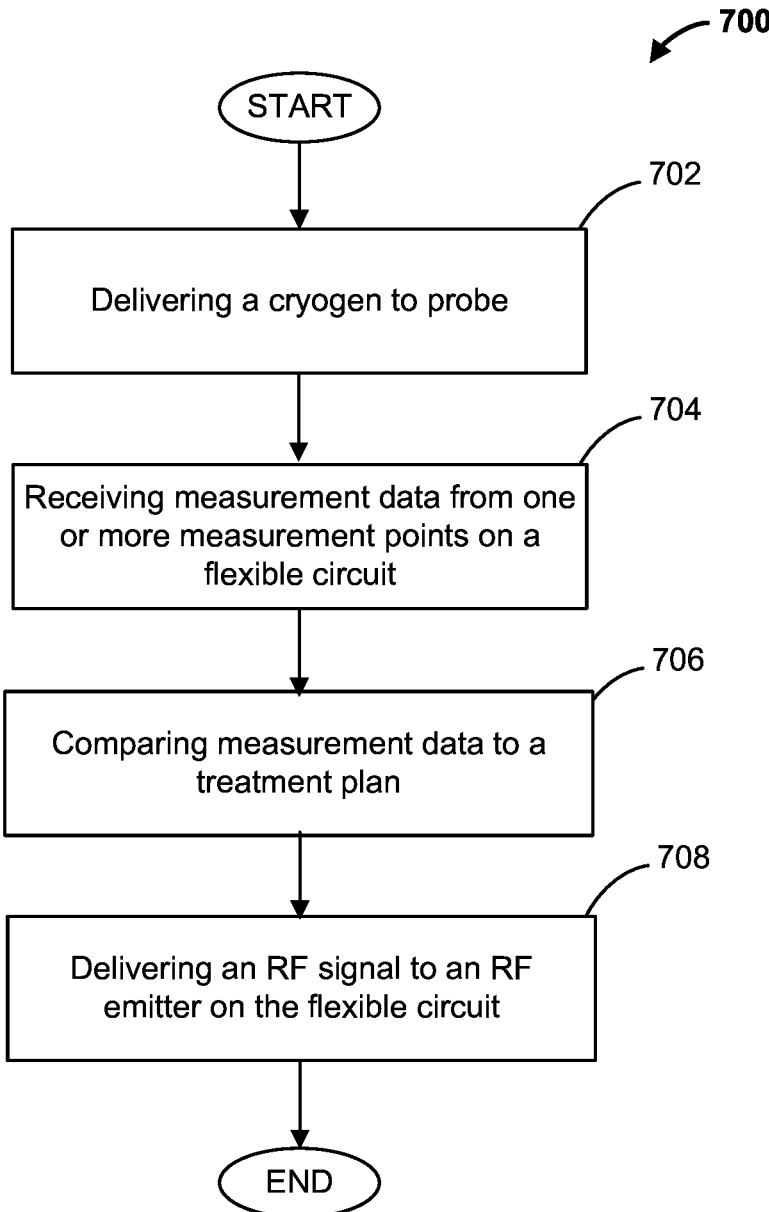
FIG. 7 is a flow chart illustrating an example method of performing an ablation treatment in accordance with some embodiments of the present disclosure.

Turning now to FIG. 7, an example method 700 of performing an ablation treatment is shown. In this example, one or more of the probes of the present disclosure and/or the ablation system 100 may be used. While other systems and probes may be used, the method is described below with reference to the ablation 100 and the probes 102, 200. It should be appreciated, however, that the method 700 is not limited to the systems, probes, and/or flexible circuits references below.

The method 700 may begin at step 702. At step 702, the ablation controller 104 may deliver cryogen to the probe 102. The ablation controller 104 may cause cryogen to flow through the cryogen path to the probe 102. This may start a freezing cycle in which ice forms at the target tissue. As can be appreciated, the probe 102 may be inserted at or near a target tissue in a patient 120 prior to the initiation of step 702.

At step 704, the ablation controller 104 may receive measurement data from one or measurement points on a flexible circuit of the probe 102. The measurement points may be configured in various suitable arrangements or configurations, such as those shown on FIGS. 5 and 6. The measurement points on the flexible circuit may provide temperature, pressure, impedance, and/or other measurement data to the ablation controller 104 and/or to the ablation computing device 106.

At step 706, the ablation controller 104 and/or the ablation computing device 106 may compare the measurement data to a treatment plan. The treatment plan may have been determined prior to the treatment depending on the needs of the patient, tissue type, tissue location, and the like. The treatment plan may include various thresholds, ranges, cycle times, duty cycles, signal profiles and the like that can characterize ablation freezing cycles, RF cycles, heating, and the like. The treatment plan may also include information to characterize identifying characteristics of a bleeding condition or other tissue conditions.

At step 708, the ablation controller 104 and/or the ablation computing device 106 may deliver an RF signal to an RF emitter located on the flexible circuit. the RF emitter may be an RF electrode, RF heater, resistive heater, microwave antenna, or the like. The RF signal may have a specified duty cycle, frequency, pulse width, duration, power, frequency, current or other characteristic to provide the desired heating, coagulation or heating that may be desired. The characteristics of the RF signal may be specified in the treatment plan, in some examples.

The RF signal may be provided to perform an RF ablation cycle in some examples. The RF signal may alternatively be provided to perform a coagulation process. The RF signal may alternatively be provided to perform a thaw process to assist in removal of the probe 102 following a cryo ablation treatment. The RF signal may also be provided to perform a pain relief or stimulation treatment.

As can be seen, the method 700 may include both cryo and RF cycles, procedures and/or treatments. The cryo and RF operations may be provided during one treatment or a common treatment.

The description above is provided for illustration and it should be appreciated that the methods and processes described are not limited to the order and to the exact performance described above. Other methods can also be performed that vary the order of the steps. In addition, other methods may not include all the steps shown and described and/or may include additional steps.

Figure 8:
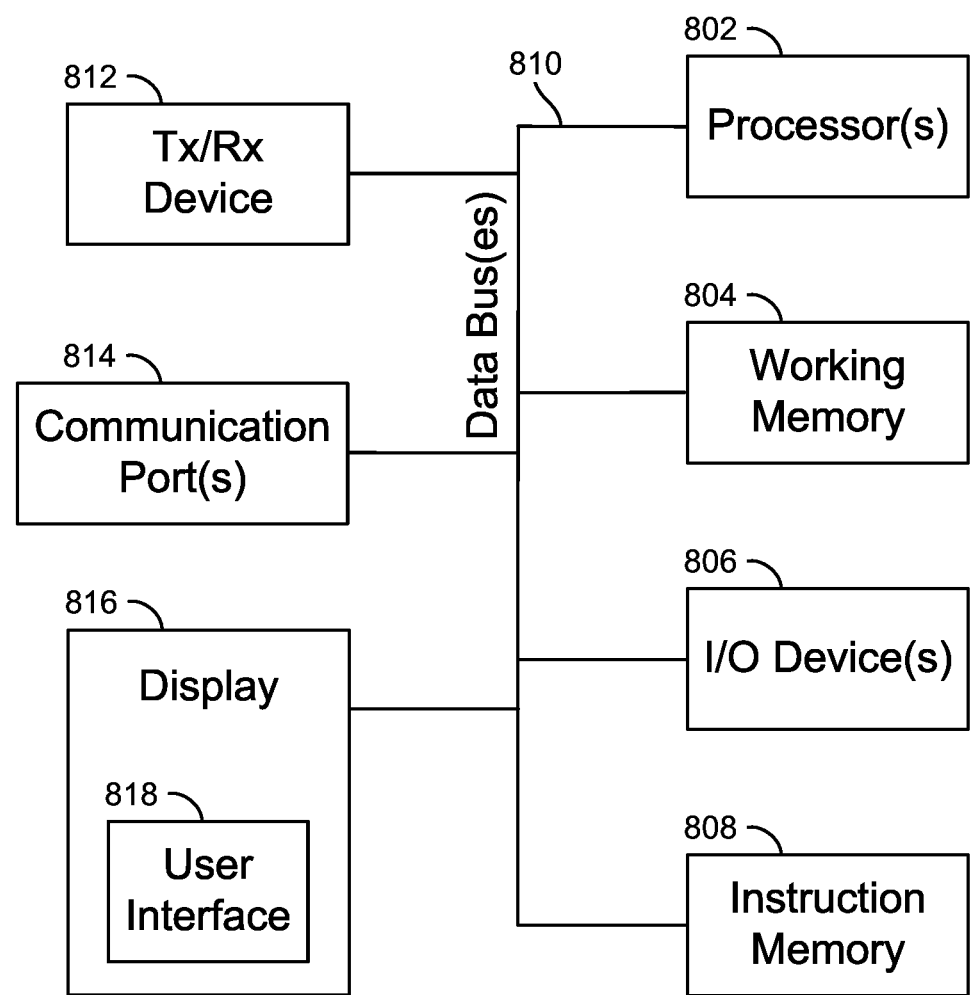
FIG. 8 is a diagram showing an example computing device that may be used in accordance with some embodiments of the present disclosure.

Referring now to FIG. 8, an example computing device 800 is shown. The ablation system 100 may include one or more computing devices 800. For example, the ablation computing device 106 may have the elements shown in FIG. 8. The methods of the present disclosure, such as method 700, may be performed, or steps of such methods may be performed, by a computing device 800.

As shown, the computing device 800 may include one or more processors 802, working memory 804, one or more input/output devices 806, instruction memory 808, a transceiver 812, one or more communication ports 814, and a display 816, all operatively coupled to one or more data buses 810. Data buses 810 allow for communication among the various devices. Data buses 810 can include wired, or wireless, communication channels.

Processors 802 can include one or more distinct processors, each having one or more cores. Each of the distinct processors can have the same or different structure. Processors 802 can include one or more central processing units (CPUs), one or more graphics processing units (GPUs), application specific integrated circuits (ASICs), digital signal processors (DSPs), and the like.

Processors 802 can be configured to perform a certain function or operation by executing code, stored on instruction memory 808, embodying the function or operation. For example, processors 802 can be configured to perform one or more of any function, step, method, or operation disclosed herein.

Instruction memory 808 can store instructions that can be accessed (e.g., read) and executed by processors 802. For example, instruction memory 808 can be a non-transitory, computer-readable storage medium such as a read-only memory (ROM), an electrically erasable programmable read-only memory (EEPROM), flash memory, a removable disk, CD-ROM, any non-volatile memory, or any other suitable memory.

Processors 802 can store data to, and read data from, working memory 804. For example, processors 802 can store a working set of instructions to working memory 804, such as instructions loaded from instruction memory 808. Processors 802 can also use working memory 804 to store dynamic data created during the operation of ablation computing device 106. Working memory 804 can be a random access memory (RAM) such as a static random access memory (SRAM) or dynamic random access memory (DRAM), or any other suitable memory.

Input-output devices 806 can include any suitable device that allows for data input or output. For example, input-output devices 806 can include one or more of a keyboard, a touchpad, a mouse, a stylus, a touchscreen, a physical button, a speaker, a microphone, or any other suitable input or output device.

Communication port(s) 814 can include, for example, a serial port such as a universal asynchronous receiver/transmitter (UART) connection, a Universal Serial Bus (USB) connection, or any other suitable communication port or connection. In some examples, communication port(s) 814 allows for the programming of executable instructions in instruction memory 808. In some examples, communication port(s) 814 allow for the transfer (e.g., uploading or downloading) of data, such as measurement data and the like.

Display 816 can display a user interface 818. User interfaces 818 can enable user interaction with the ablation computing device 106. For example, user interface 818 can be a user interface that allows an operator to interact, communicate, control and/or modify different messages, settings, or features that may be presented or otherwise displayed to a user. The user interface 818 can include a slider bar, dialogue box, or other input field that allows the user to control, communicate or modify a setting, limitation or input that is used in a cryoablation treatment. In addition, the user interface 818 can include one or more input fields or controls that allow a user to modify or control optional features or customizable aspects of the ablation computing device 106 and/or the operating parameters of the ablation system 100. In some examples, a user can interact with user interface 818 by engaging input-output devices 806. In some examples, display 816 can be a touchscreen, where user interface 818 is displayed on the touchscreen. In other examples, display 816 can be a computer display that can be interacted with using a mouse or keyboard.

Transceiver 812 allows for communication with a network. In some examples, transceiver 812 is selected based on the type of communication network ablation computing device 106 will be operating in. Processor(s) 802 is operable to receive data from, or send data to, a network, such as wired or wireless network that couples the elements of the ablation system 100.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A probe for performing an ablation treatment comprising: a shell defining an outer surface; a cryogen supply conduit positioned in the shell; and a flexible circuit board comprising a flexible substrate and a plurality of measurement points coupled to the flexible substrate, wherein the flexible substrate is positioned on at least a portion of the outer surface of the shell, and wherein the outer surface of the shell is exposed between portions of the flexible substrate.

2. The probe of claim 1, wherein the flexible circuit board comprises at least one radio frequency (RF) emitter coupled to the flexible substrate that is configured to deliver RF energy to a target tissue.

3. The probe of claim 1, wherein the plurality of measurement points is configured to obtain measurement data during the ablation treatment.

4. The probe of claim 1, wherein the flexible circuit board comprises a plurality of heaters coupled to the flexible substrate.

5. The probe of claim 1, wherein the flexible substrate covers at least about 50% of the exterior surface of the probe.

6. The probe of claim 1, wherein the flexible circuit board comprises an RF emitter configured to thaw an iceball formed during a freezing cycle of the ablation treatment.

7. The probe of claim 1, wherein the flexible circuit board comprises an RF emitter configured to perform a coagulation treatment of a bleeding condition.

8. The probe of claim 1, wherein:
the flexible circuit board is a first flexible circuit board comprising a first flexible substrate positioned at a first axial position on the shell;
the probe further comprises a second flexible circuit board comprising a second flexible substrate positioned at a second axial position on the shell; and
the first flexible substrate is separated from the second flexible substrate.

9. The probe of claim 1, wherein the cryogen supply conduit defines an inflow path for a cooling path, and an outer surface of the supply conduit and an inner surface of the shell defines an outflow path.

10. The probe of claim 1, wherein the cryogen supply conduit is configured to move liquid or gaseous nitrogen through the probe.

11. The probe of claim 1, wherein the flexible circuit board comprises a plurality of RF electrodes.

12. The probe of claim 1, further comprising a microwave antenna.

13. An ablation system comprising:

an ablation controller coupled to the probe of claim 1, the ablation controller comprising at least one processor configured to deliver a cryogen to the cryogen supply conduit and to deliver an RF signal to an RF emitter on the flexible circuit.

14. A method comprising: delivering a cryogen to a probe to perform a freezing cycle of an ablation treatment; obtaining measurement data from one or more measurement points mounted on a flexible substrate of a flexible circuit, the flexible substrate positioned on an outer surface of the probe, wherein the outer surface of the probe is exposed between portions of the flexible substrate; and delivering a radio frequency (RF) signal to an RF emitter on the flexible circuit.

15. The method of claim 14, wherein the steps of the method are performed during a common treatment.

16. The method of claim 14, wherein the radio frequency (RF) emitter comprises an RF electrode.

17. The method of claim 14, wherein the radio frequency (RF) emitter comprises a heater.

18. The method of claim 14, wherein the step of delivering the RF signal comprises performing a coagulation treatment.

19. The method of claim 14, wherein the step of delivering the RF signal comprises ablating a target tissue.

\* \* \* \* \*